(12) United States Patent
Waliwitiya

(10) Patent No.: US 9,018,392 B1
(45) Date of Patent: Apr. 28, 2015

(54) COMPOUNDS, COMPOSITIONS AND METHODS FOR CROP ENHANCEMENT

(71) Applicant: Active AgriProducts Inc., Abbotsford (CA)

(72) Inventor: Ranil Waliwitiya, Surrey (CA)

(73) Assignee: Active AgriProducts Inc., Abbotsford (CA)

( * ) Notice: Subject to any disclaimer, the term of this patent is extended or adjusted under 35 U.S.C. 154(b) by 0 days.

(21) Appl. No.: 14/258,616

(22) Filed: Apr. 22, 2014

(51) Int. Cl.
| | | |
|---|---|---|
| C07D 235/08 | (2006.01) | |
| A01N 43/52 | (2006.01) | |
| C07D 235/26 | (2006.01) | |
| C05G 3/00 | (2006.01) | |

(52) U.S. Cl.
CPC .............. *A01N 43/52* (2013.01); *C07D 235/26* (2013.01); *C05G 3/00* (2013.01); *C07D 235/08* (2013.01)

(58) Field of Classification Search
USPC ...................................... 548/304.4
See application file for complete search history.

(56) References Cited

U.S. PATENT DOCUMENTS

| | | | |
|---|---|---|---|
| 5,939,356 | A | 8/1999 | Wellinghoff |
| 7,687,638 | B2 * | 3/2010 | Feng et al. ................. 548/304.4 |
| 8,507,408 | B2 | 8/2013 | Sianawati |
| 8,507,409 | B2 | 8/2013 | Sianawati |
| 8,524,636 | B2 | 9/2013 | Soamawati |
| 8,597,395 | B2 | 12/2013 | Goodwin |
| 8,614,165 | B2 | 12/2013 | Goodwin |
| 2005/0220834 | A1 | 10/2005 | Wang |
| 2011/0053771 | A1 | 3/2011 | Goodwin |
| 2011/0077155 | A1 | 3/2011 | Goodwin |
| 2012/0165191 | A1 | 6/2012 | Sianawati et al. |
| 2012/0165192 | A1 | 6/2012 | Sianawati |
| 2012/0165297 | A1 | 6/2012 | Sianawati |

FOREIGN PATENT DOCUMENTS

| | | |
|---|---|---|
| EP | 1216976 A2 | 6/2002 |
| WO | 2013106724 A1 | 7/2013 |
| WO | 2013110258 A1 | 8/2013 |

* cited by examiner

*Primary Examiner* — Laura L. Stockton (74) *Attorney, Agent, or Firm* — Oyen Wiggs Green & Mutala LLP (57) ABSTRACT

A novel compound, 1,2-dimethyl-4-dimethylaminomethyl-5-hydroxy benzimidazole, an agriculturally acceptable salt thereof, and an agriculturally acceptable solvate thereof, for crop enhancement is provided. Related compositions and methods are also provided.

12 Claims, 12 Drawing Sheets

WHEAT (RL & RSA)-MARA

| Treatment | Root length (cm) | Root surface area (cm$^2$) | %increase (RL) | %increase (RSA) |
|---|---|---|---|---|
| Control | 66.9 | 15.2 | | |
| Intrinsic 20ppm | 83.7 | 24.5 | 25.1 | 61.2 |
| Intrinsic 40ppm | 86.2 | 25.8 | 28.8 | 69.7 |
| Intrinic 20ppm+Cmaxx | 88.4 | 26.7 | 32.1 | 75.7 |
| Intrinic 40ppm+Cmaxx | 88.6 | 26.4 | 32.4 | 73.7 |
| Intrinic 20ppm+Div | 84.3 | 24.8 | 26.0 | 63.2 |
| Intrinic 40ppm+Div | 85.1 | 26.2 | 27.2 | 72.4 |

WHEAT (shoot & root weights)-MARA

| Treatment | shoot (g) | Root (g) | shoot/root |
|---|---|---|---|
| Control | 3.6 | 0.3 | 12.0 |
| Intrinsic 20ppm | 7.3 | 0.6 | 12.2 |
| Intrinsic 40ppm | 7.45 | 0.68 | 11.0 |
| Intrinic 20ppm+Cmaxx | 7.68 | 0.73 | 10.5 |
| Intrinic 40ppm+Cmaxx | 7.71 | 0.73 | 10.6 |
| Intrinic 20ppm+Div | 7.54 | 0.69 | 10.9 |
| Intrinic 40ppm+Div | 7.62 | 0.71 | 10.7 |

Fig. 6(c)

CANOLA (RL & RSA)-SARDA

| Treatment | Root length (cm) | Root surface area (cm²) | %increase (RL) | %increase (RSA) |
|---|---|---|---|---|
| Control | 52.7 | 4.1 | | |
| Intrinsic 20ppm | 104.9 | 9.1 | 99.1 | 122.0 |
| Intrinsic 40ppm | 88.5 | 7.8 | 67.9 | 90.2 |

CANOLA (shoot & root weights)-SARDA

| Treatment | shoot (g) | Root (g) | shoot/root |
|---|---|---|---|
| Control | 5.95 | 0.81 | 9.6 |
| Intrinsic 20ppm | 10.8 | 1.49 | 7.2 |
| Intrinsic 40ppm | 16.49 | 2.23 | 7.4 |

Fig. 7(c)

CANOLA (RL & RSA)-AGQUEST

| Treatment | Root length (cm) | Root surface area (cm²) | %increase (RL) | %increase (RSA) |
|---|---|---|---|---|
| Control | 17.2 | 2.5 | | |
| Intrinsic 20ppm | 39.7 | 3.9 | 130.8 | 56.0 |
| Intrinsic 40ppm | 37.7 | 4 | 119.2 | 60.0 |

CANOLA (shoot & root weights)-AGQUEST

| Treatment | shoot (g) | Root (g) | shoot/root | |
|---|---|---|---|---|
| Control | 10.4 | 0.99 | | 10.5 |
| Intrinsic 20ppm | 9.9 | 1.1 | | 9.0 |
| Intrinsic 40ppm | 15.4 | 1.5 | | 10.3 |

Fig. 8(c)

| Treatment | Bushels/acre |
|---|---|
| Control | 77 |
| Intrinsic 40ppm | 82 |
| CruiserMaxx | 79 |
| Intrinsic 40ppm+CruiserMaxx | 83 |

| Treatment | Yield (kg/ha) | Yield increase (kg/ha) |
|---|---|---|
| Control | 4570 | |
| Intrinsic 20ppm | 4850 | 280 |
| Intrinsic 40ppm | 4844 | 274 |

COMPOUNDS, COMPOSITIONS AND METHODS FOR CROP ENHANCEMENT

TECHNICAL FIELD

This invention relates to novel compounds, compositions and methods for crop enhancement.

BACKGROUND

Increasing human population and decreasing supply of arable land necessitates effective compounds, compositions and methods for crop enhancement.

SUMMARY

The inventions described herein have many aspects, some of which relate to compounds, compositions and methods for crop enhancement.

One aspect relates to the novel compound 1,2-dimethyl-4-dimethylaminomethyl-5-hydroxy benzimidazole, an agriculturally acceptable salt thereof, and an agriculturally acceptable solvate thereof.

Another aspect relates to a composition comprising 1,2-dimethyl-4-dimethylaminomethyl-5-hydroxy benzimidazole, an agriculturally acceptable salt thereof, or an agriculturally acceptable solvate thereof; and an agriculturally acceptable carrier.

Another aspect relates to a method of treating a plant, the method comprising exposing the plant to an effective amount of 1,2-dimethyl-4-dimethylaminomethyl-5-hydroxy benzimidazole, an agriculturally acceptable salt thereof, or an agriculturally acceptable solvate thereof. Exposing the plant may comprise spray treatment, soil treatment, seed treatment and/or hydroponic treatment. The method may further comprise exposing the plant to a fertilizer, such as a fertilizer selected from the group consisting of the following combinations: nitrogen (4%), phosphorous (P2O5) (18%), potassium (K2O) (6%), zinc (1%), manganese (1%), boron (0.05%), and copper (0.1%), nitrogen (2%), phosphorous (P2O5) (30%), potassium (K2O) (6%), zinc (3%), manganese (1%), boron (1%), and copper (1%); and nitrogen (0%), phosphorous (P2O5) (38%), potassium (K2O) (8%), zinc (5%), manganese (2%), and copper (1%). The plant may be wheat, corn, canola or soybean. The compound may be formulated in an aqueous solution and the solution applied at a concentration of 10 to 50 ppm. The method may be adapted to enhance input use efficiency, improve plant quality, improve plant vigor, improve plant yield and/or an improve tolerance to stress factors.

The foregoing discussion merely summarizes certain aspects of the inventions and is not intended, nor should it be construed, as limiting the inventions in any way.

BRIEF DESCRIPTION OF DRAWINGS

The following drawings show non-limiting embodiments of the invention.

FIG. 1 shows photographs of the effects of a composition according to an embodiment on wheat seed germination at (a) 24 hours after treatment; (b) 48 hours after treatment; (c) 72 hours after treatment and (d) 96 hours after treatment.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

The term "agriculturally acceptable carrier" as used herein refers to a carrier that is not unacceptably damaging to a plant or its environment, and/or not unsafe to the user or others that may be exposed to the material when used as described herein. For example, an agriculturally acceptable carrier may be a solid carrier, a gel carrier, a liquid carrier, a suspension, or an emulsion. Agriculturally acceptable carriers may include, for example, adjuvants, inert components, dispersants, surfactants, tackifiers, binders, and/or stabilizers.

The term "agriculturally acceptable salt" as used herein refers to a salt that retains the biological effectiveness of the free acids and bases of the compounds described and disclosed herein and that are not unacceptably damaging to a plant or its environment, and/or not unsafe to the user or others that may be exposed to the material when used as described herein. Examples of agriculturally acceptable salts include acetates, acrylates, benzoates, bisulfates, bisulfites, bromides, butyrates, caprylates, chlorides, citrates, decanoates, formats, fumarates, glycolates, heptanoates, iodides, lactates, maleates, malonates, oxalates, phosphates, phthalates, propionates, pyrosulfates, succinates, sulfates, sulfites, sulfonates, and tartrates.

The term "agriculturally acceptable solvate" as used herein refers to an association of one or more solvent molecules and the compounds described and disclosed herein, wherein the solvent is not unacceptably damaging to a plant or its environment, and/or not unsafe to the user or others that may be exposed to the material when used as described herein. A non-limiting example of a solvent that forms agriculturally acceptable solvates is water.

The term "crop enhancement" as used herein means an improvement in input use efficiency, an improvement in plant quality, an improvement in plant vigor, an improvement in plant yield and/or an improvement in tolerance to stress factors.

The term "improvement in input use efficiency" and the like as used herein means that the plants are able to grow more effectively using given levels of inputs compared to the growth of control plants which are grown under the same conditions in the absence of the application of the compounds, compositions and/or methods described and disclosed herein. In particular, the inputs include, but are not limited to fertilizers (such as nitrogen, phosphorous, potassium, micronutrients), light and water. A plant with improved input use efficiency may have an improved use of any of the aforementioned inputs or any combination of two or more of the aforementioned inputs.

The term "improvement in plant quality" and the like as used herein means that certain traits are improved qualitatively or quantitatively when compared with the same trait in a control plant which has been grown under the same conditions in the absence of the application of the compounds, compositions and/or methods described and disclosed herein. Such traits include, but are not limited to, improved visual appearance of the plant, improved quality of harvested material, e.g. seeds, fruits, leaves, vegetables (such improved quality may manifest as improved visual appearance of the harvested material, improved carbohydrate content (e.g. increased quantities of sugar and/or starch, improved sugar acid ratio, reduction of reducing sugars, increased rate of development of sugar), improved protein content, improved oil content and composition, improved nutritional value, reduction in anti-nutritional compounds, improved organoleptic properties (e.g. improved taste) and/or improved consumer health benefits (e.g. increased levels of vitamins and anti-oxidants)), improved post-harvest characteristics (e.g. enhanced shelf-life and/or storage stability, easier processability, easier extraction of compounds) and/or improved seed quality (e.g. for use in following seasons). A plant with improved quality may have an increase in any of the aforementioned traits or any combination or two or more of the aforementioned traits.

The term "improvement in plant vigor" and the like as used herein means that certain traits are improved qualitatively or quantitatively when compared with the same trait in a control plant which has been grown under the same conditions in the absence of the application of the compounds, compositions and/or methods described and disclosed herein. Such traits include, but are not limited to, improved plant vitality of the plant; improved plant growth; improved plant development; improved plant stand; improved emergence; enhanced root growth and/or more developed root system; enhanced nodulation; larger leaf blade; increased plant size; increased plant weight; increased plant height; increased and/or stronger tillers; increased shoot growth; increased yield when grown on poor soils or unfavorable climate; enhanced photosynthetic activity; earlier flowering; earlier fruiting; earlier and improved germination; earlier grain maturity; improved self-defense mechanisms; less non-productive tillers; less dead basal leaves; greener leaves; complete maturation under shortened vegetation periods; less seeds needed; faster and more uniform ripening; longer panicles; delay of senescence. A plant with improved vigor may have an increase in any of the aforementioned traits or any combination or two or more of the aforementioned traits.

The term "improvement in plant yield" and the like as used herein means that yield of a product of economic value of the plant (such as grains, fruits, vegetables, nuts, seeds) is increased by a measurable amount over the same yield in a control plant which has been grown under the same conditions in the absence of the application of the compounds, compositions and/or methods described and disclosed herein. Improvement in plant yield can for example mean one or of: (i) an increase in biomass production, grain yield, starch content, oil content and/or protein content, which may result from (a) an increase in the amount produced by the plant per se or (b) an improved ability to harvest plant matter, (ii) an improvement in the composition of the harvested material (e.g. improved sugar acid ratios, improved oil composition, increased nutritional value, reduction of anti-nutritional compounds, increased consumer health benefits) and/or (iii) an increased/facilitated ability to harvest the crop, improved processability of the crop and/or better storage stability/shelf life.

The term "improved tolerance to stress factors" and the like as used herein means that certain traits are improved qualitatively or quantitatively when compared with the same trait in a control plant which has been grown under the same conditions in the absence of the application of the compounds, compositions and/or methods described and disclosed herein. Such traits include, but are not limited to, an increased tolerance and/or resistance to abiotic stress factors which cause sub-optimal growing conditions such as drought (e.g. any stress which leads to a lack of water content in plants, a lack of water uptake potential or a reduction in the water supply to plants), cold exposure, heat exposure, osmotic stress, UV stress, flooding, increased salinity (e.g. in the soil), increased mineral exposure, ozone exposure, high light exposure and/or limited availability of nutrients (e.g. nitrogen and/or phosphorus nutrients). A plant with improved tolerance to stress factors may have an increase in any of the aforementioned traits or any combination or two or more of the aforementioned traits. In the case of drought and nutrient stress, such improved tolerances may be due to, for example, more efficient uptake, use or retention of water and nutrients.

The term "locus" as used herein refers to an area in proximity to a plant or the area in which seed is or can be sown.

The term "plant" as used herein refers to plants of economic importance, and in particular agricultural plants. The term "plant" includes food crops (such as, broad-leaved field crops (e.g. soybean), cereal crops (e.g. corn, millet, oats, wheat), fruit crops, seed crops (e.g. canola) and vegetable crops, as for example set out in WO 2013/106724, which is incorporated by reference herein in its entirety); silviculture crops (for example, timber crops); household, garden, ornamental and nursery plants (for example, chrysanthemums, carnations, daffodils, marigolds, petunias, roses, snapdragons, tulips); and other plants of economic significance such as hops, sugar cane, sugar beet, tobacco, and the like. The term "plant" as used herein encompasses whole plants, shoot vegetative organs/structures (for example, leaves, stems and tubers), roots, flowers and floral organs/structures (for example, bracts, sepals, petals, stamens, carpels, anthers and ovules), seed, plant tissue (for example, vascular tissue, ground tissue, and the like) and cells (for example, guard cells, egg cells, epidermal cells, mesophyll cells, protoplasts, and the like), and progeny of same.

The term "seed" as used herein refers to seeds and plant propagules of all kinds including but not limited to true seeds, seed pieces, suckers, corms, bulbs, fruit, tubers, grains, cuttings, cut shoots and the like.

The term "seed treatment" as used herein refers to all suitable seed treatment techniques known in the art, such as seed dressing, seed coating, seed dusting, seed soaking, seed impregnation and seed pelleting.

One aspect relates to the novel compound 1,2-dimethyl-4-dimethylaminomethyl-5-hydroxy benzimidazole, agriculturally acceptable salts thereof, or agriculturally acceptable solvates thereof.

Without being bound to any theory, it is believed that the compounds described and disclosed herein improve nutrient availability inside plants, improve nutrient mobility inside the plants, improve plant hormone synthesis, improve plant hormone availability, and/or provide synergistic actions with plant hormones. The foregoing are believed to result from the compounds described and disclosed herein triggering or altering gene expression relating to plant growth, development, stress tolerance, and/or disease resistance.

Another aspect relates to a composition comprising the compounds described and disclosed herein and an agriculturally acceptable carrier. In some embodiments the compositions comprise from 0.0001% to 99% by weight, or from 0.0001% to 95% by weight, of the compounds described and disclosed herein, and 1 to 99.9% by weight of an agriculturally acceptable carrier.

In some embodiments the compounds and compositions disclosed and described herein can be provided in concentrate form, (e.g., liquid, gel, or reconstitutable powder form), suitable for further dilution and/or mixing in water prior to application to the seed, plant, or locus. In some embodiments, the compounds and compositions disclosed and described herein can be provided as a ready-to-use solution for direct application. Because the compounds and compositions disclosed and described herein can be combined with other fertilizer solutions and/or with pesticide solutions, they can be diluted and/or reconstituted by mixing with such other solutions. In some embodiments, the compounds and compositions disclosed and described herein can be provided as a seed coating or a component of a seed coating.

A further aspect relates to methods of using the compounds and compositions disclosed and described herein for crop enhancement. In some embodiments, crop enhancement relates to enhancement of food crops. In some embodiments the methods comprise applying a compound or composition as described herein to a seed, to a foliar surface of a plant, or to a locus of the plant or seed. In some embodiments, compounds and compositions disclosed and described herein can be applied using any conventional system for applying vapor, liquid, gel or solid to a seed, to a foliar surface of a plant, or to a locus of the plant or seed.

In some embodiments the method comprises seed treatment. In some embodiments, a composition for seed treatment can be provided in concentrate form, and can be diluted up to about 1000-fold or more with water, more typically up to about 100-fold or up to about 50-fold. In some embodiments, a composition can be applied to seeds at about 0.1 to 1000 ppm, or 0.5 to 200 ppm, or 1 to 100 ppm, or 10 to 50 ppm of the compounds described and disclosed herein. 1 ppm of compound is equivalent to 1 microgram of compound per gram of seed.

In some embodiments, the method comprises spray treatment. In some embodiments, spray treatment comprises any conventional atomization method used to generate spray droplets, including hydraulic nozzles and rotating disk atomizers, for application to a foliar surface of the plant.

In some embodiments, the method comprises soil treatment. In some embodiments, soil treatment comprises any conventional technique for introducing the compounds or compositions described and disclosed herein into the soil, for example by drizzling, soil spraying, soil injection, coated granules and the like. Application in coated granule form can for example use the methods described in WO 2013/106724.

In some embodiments, the method comprises hydroponic treatment. In some embodiments, hydroponic treatment comprises introducing the compounds or compositions described and disclosed herein into the hydroponic media in which the plant is grown.

In other embodiments, the method comprises application of the compounds or compositions described and disclosed herein by other techniques such as introduction into an irrigation system, direct introduction into the plant (e.g. injection), and the like.

In some embodiments, the method comprises application of the compounds or compositions described and disclosed herein to the foliar surface or locus of the plant. The application rate of the compound or composition can be between about 0.001 gram/ha to about 100.0 gram/ha dry weight, between about 0.1 gram/ha to about 5.0 gram/ha dry weight, and between 0.5 gram/ha to about 2.0 gram/ha dry weight, applied to the foliar surface or the locus of the plant.

In some embodiments the method comprises application of the compounds or compositions described and disclosed herein in combination with one or more natural or synthetic fertilizers. In example embodiments the fertilizer may be selected from the group consisting of the following combinations: nitrogen (4%), phosphorous ($P_2O_5$) (18%), potassium ($K_2O$) (6%), zinc (1%), manganese (1%), boron (0.05%), and copper (0.1%); nitrogen (2%), phosphorous ($P_2O_5$) (30%), potassium ($K_2O$) (6%), zinc (3%), manganese (1%), boron (1%), and copper (1%); and nitrogen (0%), phosphorous ($P_2O_5$) (38%), potassium ($K_2O$) (8%), zinc (5%), manganese (2%), and copper (1%).

A still further aspect relates to seeds pre-treated with the compounds or compositions disclosed and described herein.

This application is intended to cover any variations, uses, or adaptations of the invention using its general principles. Further, this application is intended to cover such departures from the present disclosure as come within known or customary practice in the art to which this invention pertains and which fall within the limits of the appended claims. Accordingly, the scope of the claims should not be limited by the preferred embodiments set forth in the description, but should be given the broadest interpretation consistent with the description as a whole.

EXAMPLES

The invention can be further understood by reference to the following examples, which are provided by way of illustration and are not meant to be limiting.

For the Experiments described below, application of 1,2-dimethyl-4-dimethylaminomethyl-5-hydroxy benzimidazole (referred to herein as INTRINSIC™) was by way of seed treatment. Treated seeds were prepared by mixing 1.0 kg of seed and 2.0 mL of an aqueous solution of INTRINSIC™ comprising 0.1% potassium hydroxide in a ZIPLOC™ bag. Control seeds were prepared by mixing 1.0 kg of seed and 2.0 mL of aqueous 0.1% potassium hydroxide solution in a ZIPLOC™ bag. The seeds and solutions were sufficiently mixed to wet the seeds. The seeds were dried after being wetted. INTRINSIC™-treated seeds were found to maintain the activities demonstrated below for at least nine months beyond the date of treatment.

Experiment 1 (Wheat Germination)

Figure 1A:
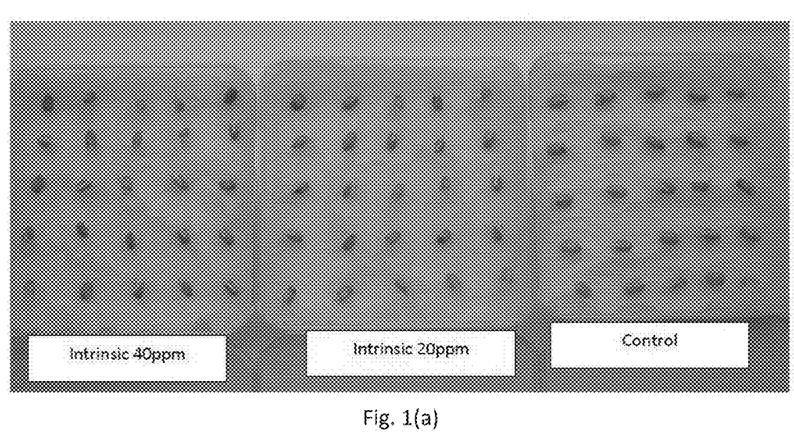
Figure 1B:
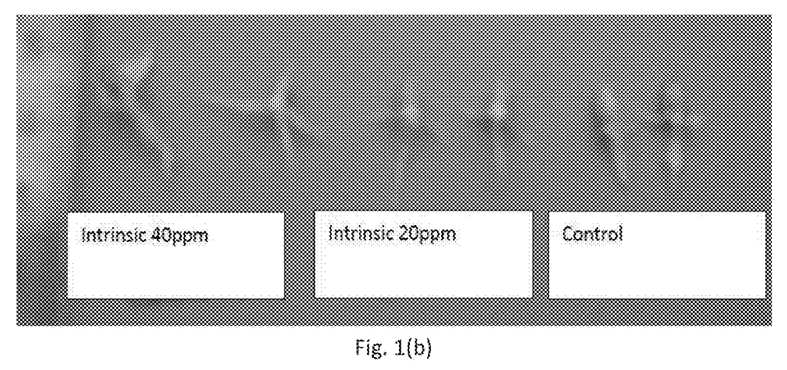
Figure 1C:
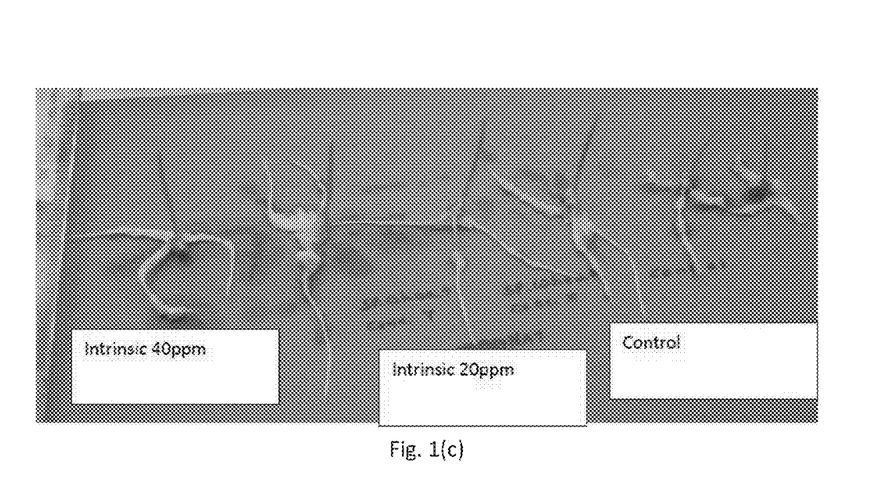
Figure 1D:
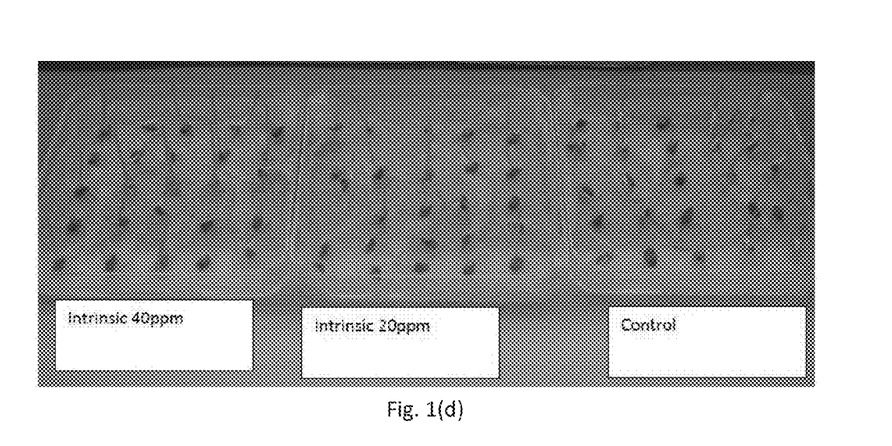

Experiment 1 tested the effects of 20 ppm and 40 ppm INTRINSIC™ on wheat seed germination under laboratory conditions. Treated and control seeds were grown in seedling trays lined with moistened tissue. The results are shown in FIGS. 1(a) to 1(d). As shown in FIG. 1(a) a greater number of treated wheat seeds compared to control wheat seeds were broken open at 24 hours. FIGS. 1(b) to 1(d) shows seedling development at 48 h, 72 h and 96 h respectively. Seedlings from treated seeds showed a greater number of roots, longer roots, and longer shoots compared to seedlings from control seeds.

Experiment 2 (Wheat Root Growth)

Figures 2A, 2B:
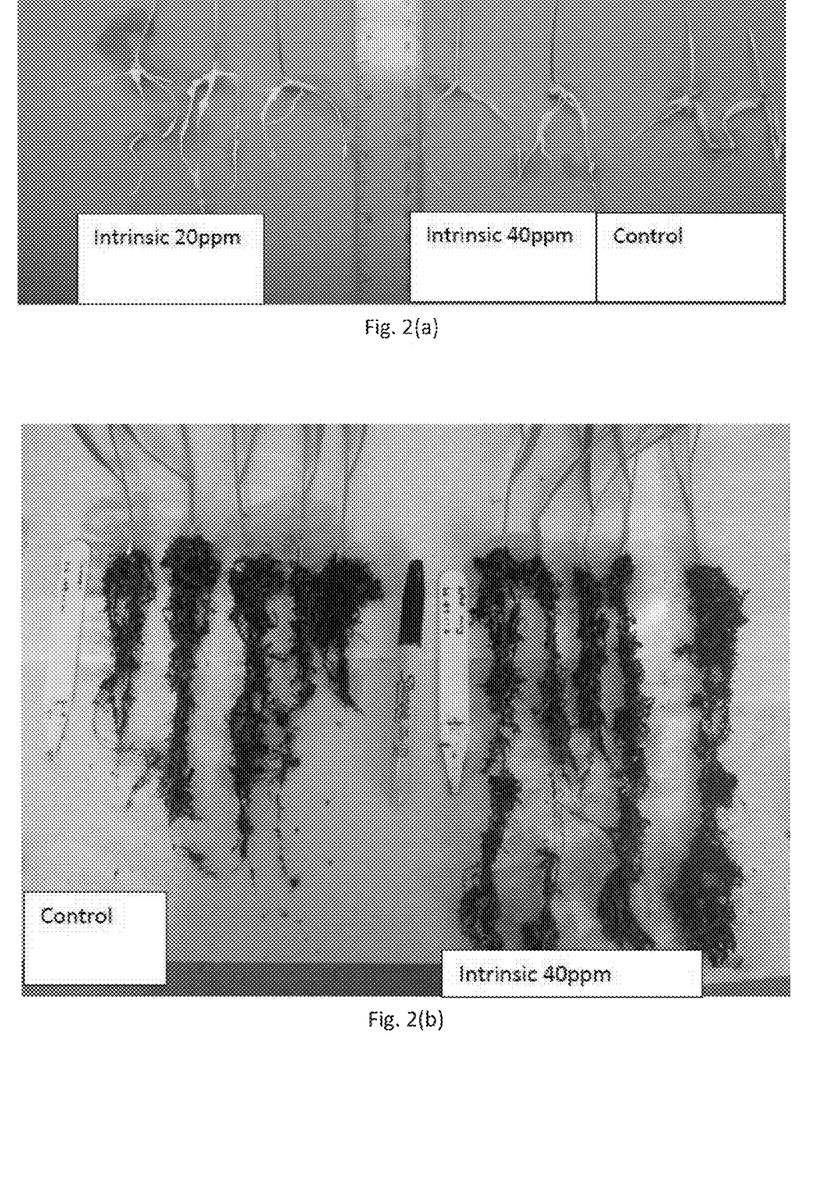
FIGS. 2(a) to (c) show photographs of the effects of a composition according to an embodiment on root growth of wheat.
Figure 2C:
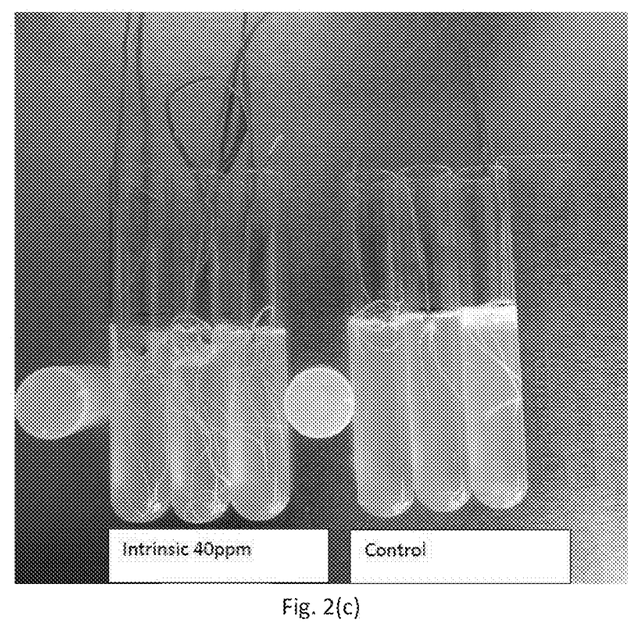

Experiment 2(a) tested the effects of 20 ppm and 40 ppm INTRINSIC™ on wheat root growth under laboratory conditions. Treated and control seeds were grown in seedling trays lined with moistened tissue. Results at 72 hours are shown in FIG. 2(a). Experiment 2(b) tested the effects of 40 ppm INTRINSIC™ on wheat root growth under greenhouse conditions. Results at 10 days are shown in FIG. 2(b). Experiment 2(c) tested the effects of 40 ppm INTRINSIC™ on wheat root growth under laboratory conditions. Treated and control seeds were grown in agar culture medium. Results at 8 days are shown Figure in FIG. 2(c). Seedlings from treated seeds in FIGS. 2(a) to 2(c) showed a greater number of roots, longer roots, and longer shoots compared to seedlings from control seeds.

Experiment 3 (Canola Root Growth)

Figure 3:
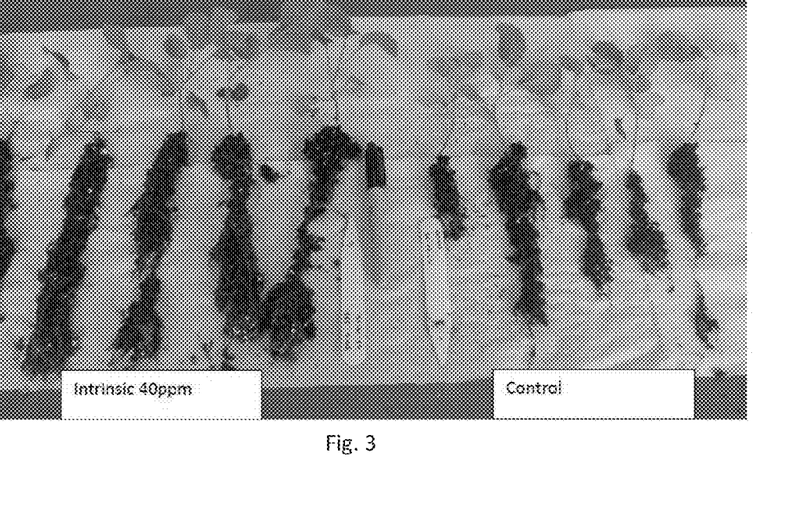
FIG. 3 shows a photograph of the effects of a composition according to an embodiment on root growth of canola.

Experiment 3 tested the effects of 40 ppm INTRINSIC™ on canola root growth under greenhouse conditions. Results 10 days are shown in FIG. 3. Seedlings from treated seeds showed a greater number of roots, longer roots, and larger foliage compared to seedlings from control seeds.

Experiment 4 (Soy Bean Root Growth)

Figure 4:
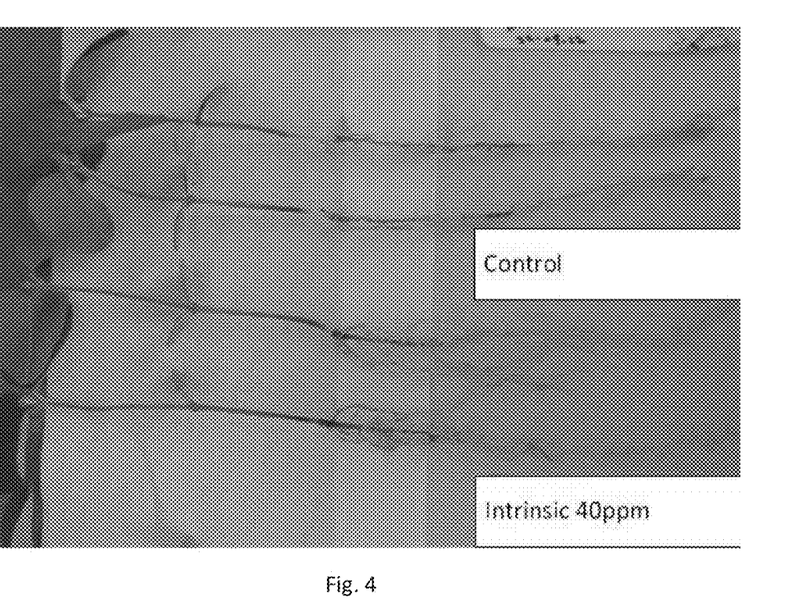
FIG. 4 shows a photograph of the effects of a composition according to an embodiment on root growth of soy bean.

Experiment 4 tested the effects of 40 ppm INTRINSIC™ on soy bean root growth under greenhouse conditions. Results 10 days are shown in FIG. 4. Seedlings from treated seeds showed a greater number of roots and larger foliage compared to seedlings from control seeds.

Experiment 5 (Corn Root Growth)

Figure 5:
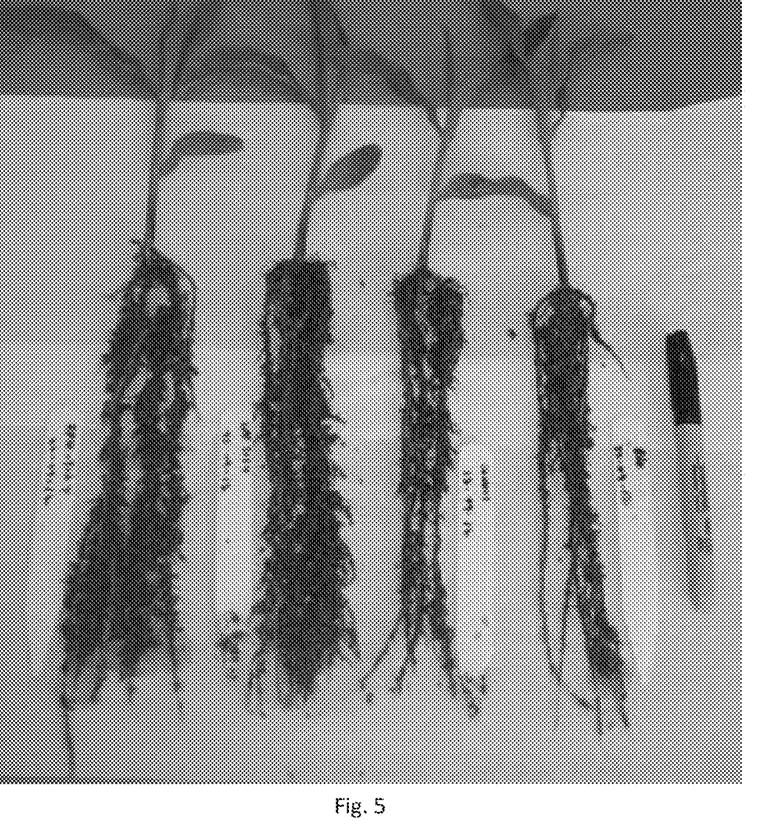
FIG. 5 shows a photograph of the effects of a composition according to an embodiment on root growth of corn.

Experiment 5 tested the effects of 40 ppm INTRINSIC™ on corn root growth under greenhouse conditions. Results 10 days are shown in FIG. 5. Seedlings from treated seeds showed a greater number of roots and larger foliage compared to seedlings from control seeds.

Experiment 6 (Wheat Growth)

Figure 6A:
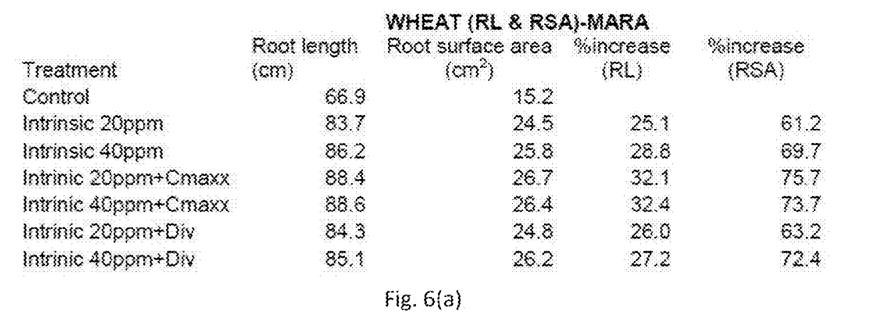
FIG. 6(a) is a table showing results of the effects of a composition according to an embodiment, alone and in combination with known commercial compositions, on root length and root surface area of wheat.
Figure 6B:
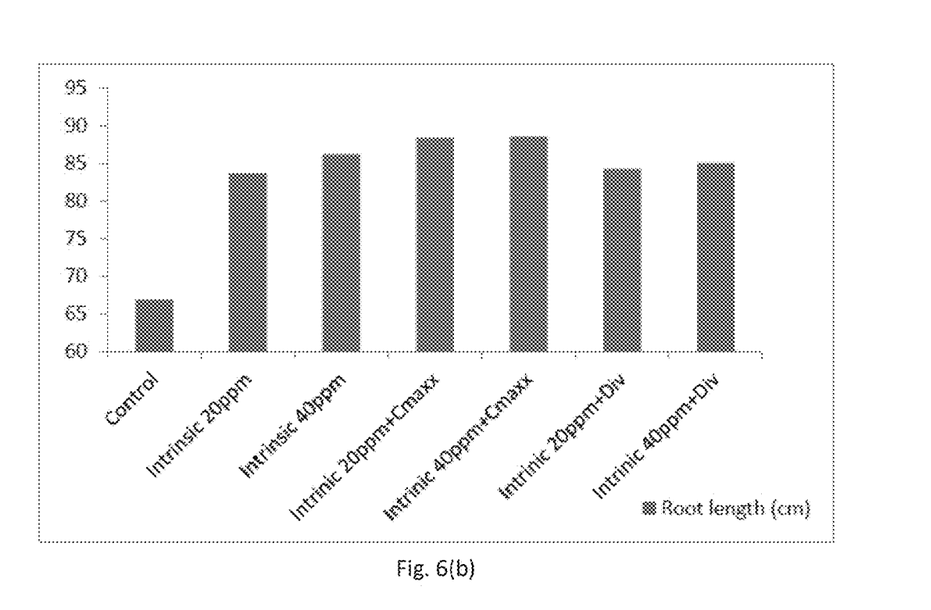
FIG. 6(b) is a graphical form of the results shown in FIG. 6(a).
Figure 6C:
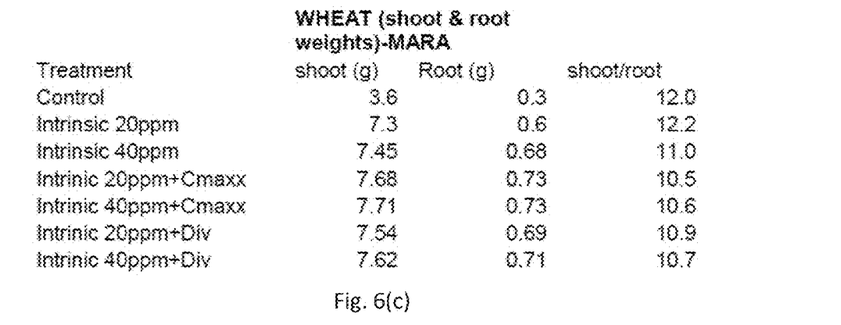
FIG. 6(c) is a table showing results of the effects of a composition according to an embodiment, alone and in combination with known compounds, on shoot weight and root weight of wheat.

Experiment 6 tested the effects of 20 ppm and 40 ppm INTRINSIC™, alone and combined with known seed treatments (CRUISER MAXX™ and DIVIDEND™, from Syngenta™ Canada Inc., applied per manufacturer's recommendations), on wheat growth under field test conditions. FIGS. 6(a) and 6(b) display results from one set of tests at 10 days, showing significant increases in root length and root surface area of seedlings from treated seeds compared to seedlings from control seeds. FIG. 6(c) display results from another set of tests at 10 days, showing significant increases in shoot weight and root weight of seedlings from treated seeds compared to seedlings from control seeds.

Experiments 7 and 8 (Canola Growth)

Experiments 7 and 8 tested the effects of 20 ppm and 40 ppm INTRINSIC™, on canola growth under field test conditions.

Figure 7A:
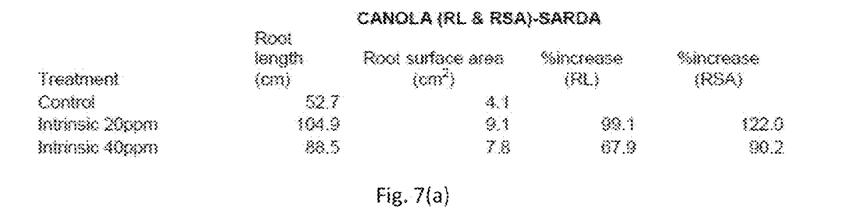
FIG. 7(a) is a table showing results of the effects of a composition according to an embodiment on root length and root surface area of canola.
Figure 7B:
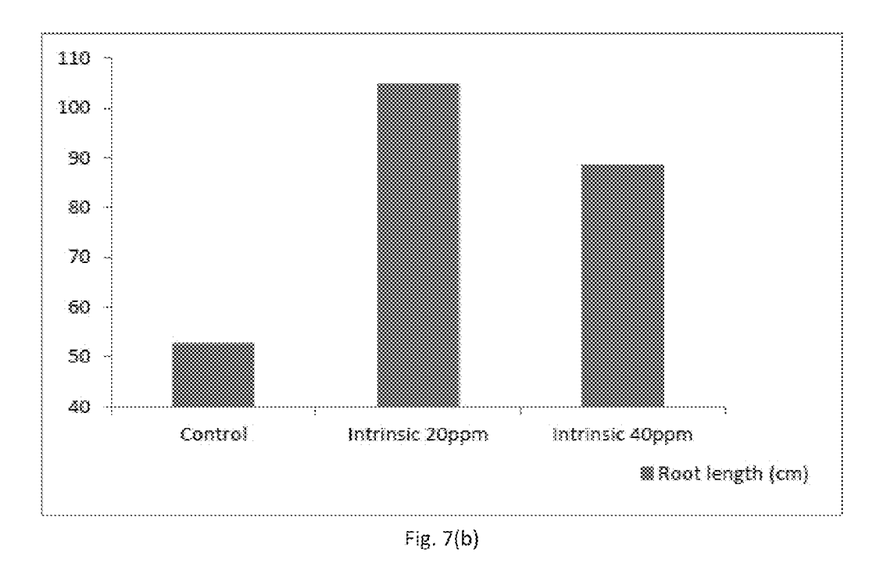
FIG. 7(b) is a graphical form of the results shown in FIG. 7(a).
Figure 7C:
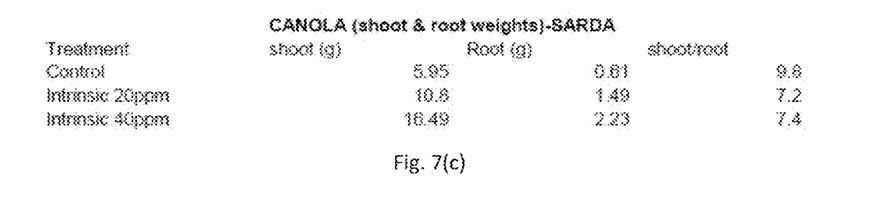
FIG. 7(c) is a table showing results of the effects of a composition according to an embodiment on shoot weight and root weight of canola.

FIGS. 7(a) and 7(b) display results from one set of tests at 10 days at a first site, showing significant increases in root length and root surface area of seedlings from treated seeds compared to seedlings from control seeds. FIG. 7(c) display results from another set of tests at 10 days at the first site, showing significant increases in shoot weight and root weight of seedlings from treated seeds compared to seedlings from control seeds.

Figure 8A:
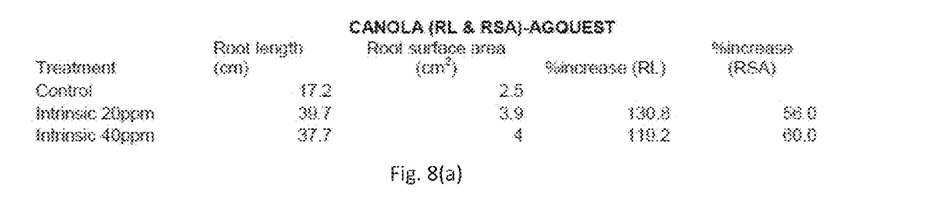
FIG. 8(a) is a table showing results of the effects of a composition according to an embodiment on root length and root surface area of canola.
Figure 8B:
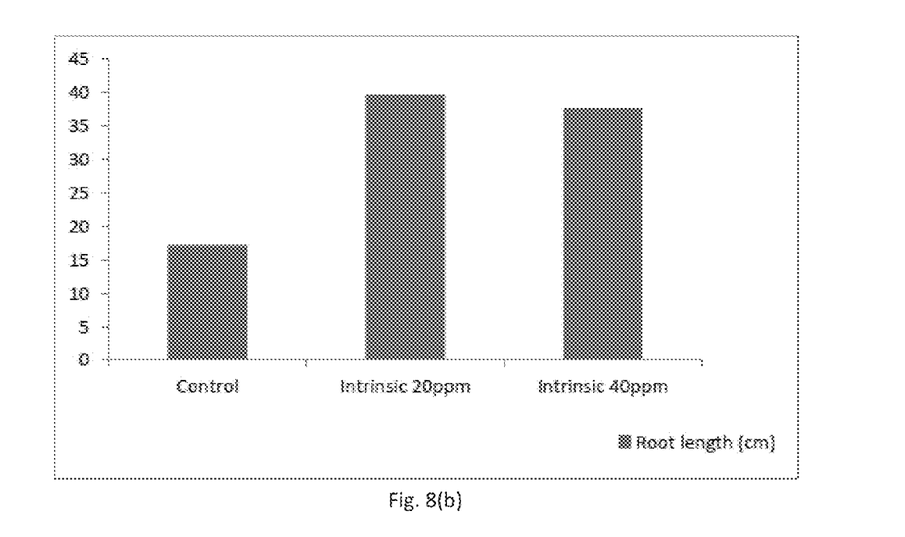
FIG. 8(b) is a graphical form of the results shown in FIG. 8(a).
Figure 8C:
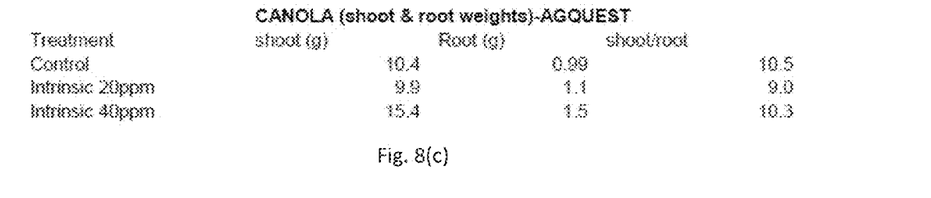
FIG. 8(c) is a table showing results of the effects of a composition according to an embodiment on shoot weight and root weight of canola.

FIGS. 8(a) and 8(b) display results from one set of tests at 10 days at a second site, showing significant increases in root length and root surface area of seedlings from treated seeds compared to seedlings from control seeds. FIG. 8(c) display results from another set of tests at 10 days at the second site, showing significant increases in shoot weight and root weight of seedlings from 40 ppm INTRINSIC™-treated seeds compared to seedlings from control seeds.

Experiment 9 (Wheat Yield)

Figure 9A:
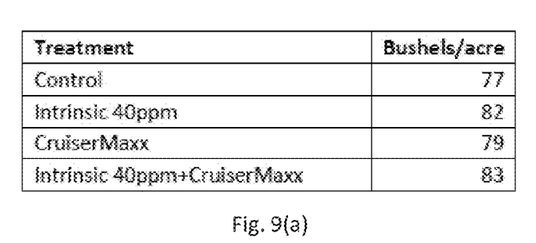
FIG. 9(a) is a table showing results of the effects of a composition according to an embodiment, alone and in combination with a known commercial composition, on yield of wheat.
Figure 9B:
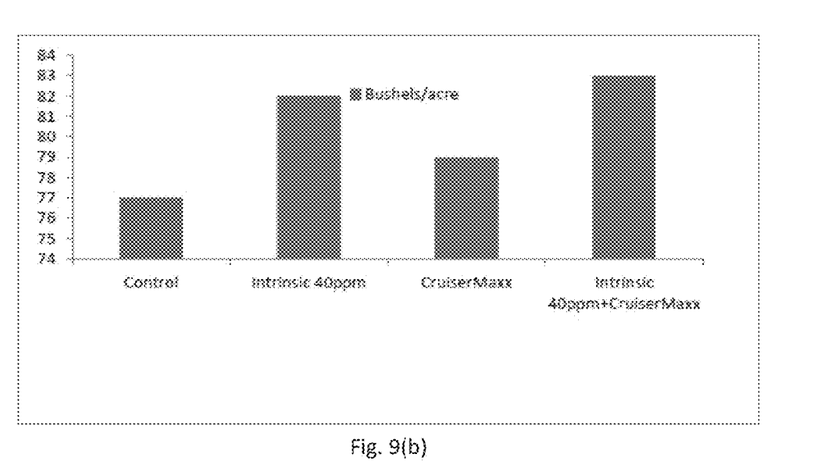
FIG. 9(b) is a graph showing same.

Experiment 9 tested the effects of 40 ppm INTRINSIC™, CRUISER MAXX™, and the combination of the two, on wheat yield under field test conditions. CRUISER MAXX™ was applied per the manufacturer's recommendations. FIGS. 9(a) and 9(b) display yield results at crop maturation (approximately 90 days), showing greater yield crops from INTRINSIC™-treated seeds (whether alone or in combination with CRUISER MAXX™) compared to crops from control seeds.

Experiments 10 and 11 (Canola Yield)

Figure 10A:
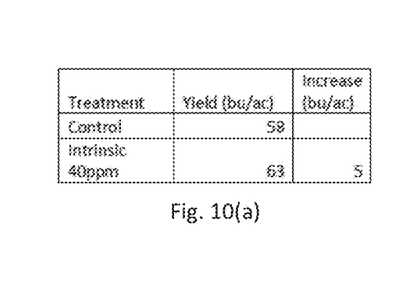
FIG. 10(a) is a table showing results of the effects of a composition according to an embodiment on yield of canola.
Figure 10B:
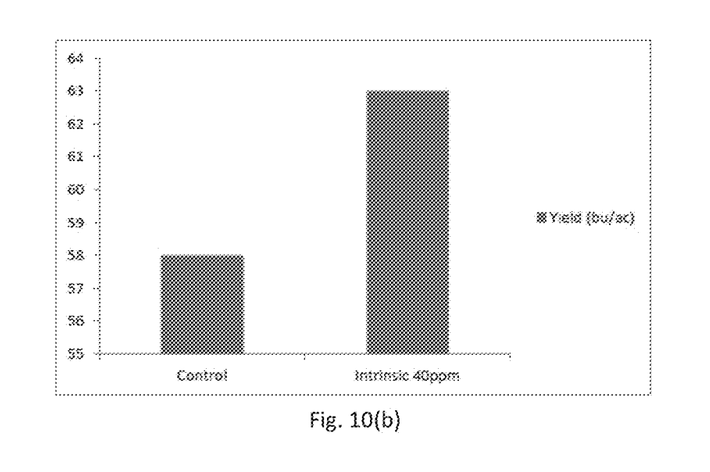
FIG. 10(b) is a graph showing same.
Figure 11A:
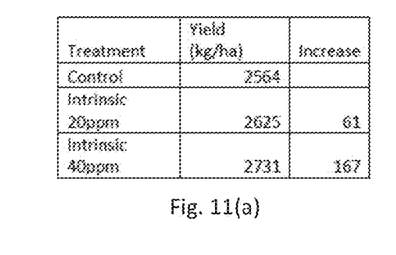
FIG. 11(a) is a table showing results of the effects of a composition according to an embodiment on yield of canola.
Figure 11B:
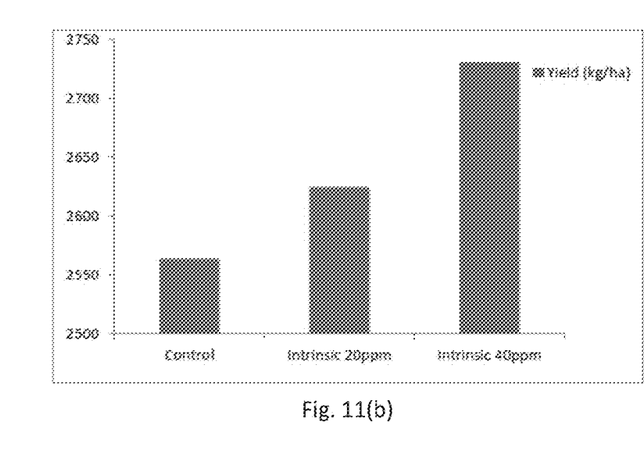
FIG. 11(b) is a graph showing same.

Experiments 10 and 11 tested the effects of 20 ppm and 40 ppm INTRINSIC™ on canola yield under field test conditions. FIGS. 10(a) and 10(b) display yield results at crop maturation (approximately 90 days) at a first site, showing greater yield crops from treated seeds compared to crops from control seeds. FIGS. 11(a) and 11(b) display yield results at crop maturation (approximately 90 days) at a second site, again showing greater yield crops from treated seeds compared to crops from control seeds.

Experiment 12 (Soy Bean Yield)

Figure 12A:
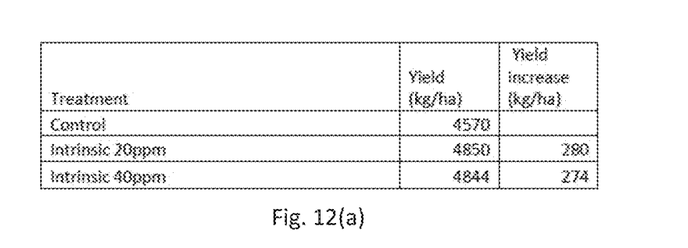
FIG. 12(a) is a table showing results of the effects of a composition according to an embodiment on yield of soy bean.
Figure 12B:
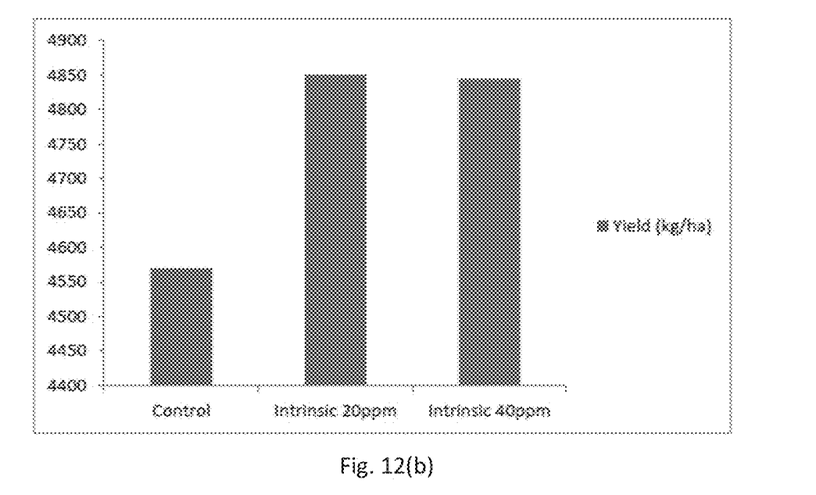
FIG. 12(b) is a graph showing same.

Experiment 12 tested the effects of 20 ppm and 40 ppm INTRINSIC™ on soy bean yield under field test conditions. FIGS. 12(a) and 12(b) display yield results at crop maturation (approximately 90 days), showing greater yield crops from treated seeds compared to crops from control seeds.

What is claimed is:

1. The compound 1,2-dimethyl-4-dimethylaminomethyl-5-hydroxy benzimidazole, an agriculturally acceptable salt thereof, or an agriculturally acceptable solvate thereof.

2. A composition comprising 1,2-dimethyl-4-dimethylaminomethyl-5-hydroxy benzimidazole, an agriculturally acceptable salt thereof, or an agriculturally acceptable solvate thereof; and an agriculturally acceptable carrier.

3. A method for crop enhancement, the method comprising exposing a plant to an effective amount of 1,2-dimethyl 4-dimethylaminomethyl-5-hydroxy benzimidazole, an agriculturally acceptable salt thereof, or an agriculturally acceptable solvate thereof.

4. The method of claim 3 wherein exposing the plant comprises spray treatment.

5. The method of claim 3 wherein exposing the plant comprises soil treatment.

6. The method of claim 3 wherein exposing the plant comprises seed treatment.

7. The method of claim 3 wherein exposing the plant comprises hydroponic treatment.

8. The method of claim 3 wherein the method further comprises exposing the plant to a fertilizer.

9. The method of claim 8, wherein the fertilizer is selected from the group consisting of the following combinations: nitrogen (4%), phosphorous (P2O5) (18%), potassium (K2O) (6%), zinc (1%), manganese (1%), boron (0.05%), and copper (0.1%); nitrogen (2%), phosphorous (P2O5) (30%), potassium (K2O) (6%), zinc (3%), manganese (1%), boron (1%), and copper (1%); and nitrogen (0%), phosphorous (P2O5) (38%), potassium (K2O) (8%), zinc (5%), manganese (2%), and copper (1%).

10. The method of claim 3 wherein the plant is wheat, corn, canola or soybean.

11. The method of claim 3 wherein the compound is formulated in an aqueous solution and the solution is applied at a concentration of 10 to 50 ppm.

12. The method of claim 3 wherein the method is adapted to enhance input use efficiency, improve plant quality, improve plant vigor, improve plant yield and/or an improve tolerance to stress factors.

\* \* \* \* \*